(12) United States Patent
Castro (10) Patent No.: US 10,772,738 B2
(45) Date of Patent: Sep. 15, 2020

(54) JOINT ARTHRODESIS SYSTEM

(71) Applicant: BLUE SKY TECHNOLOGIES, LLC, louisville, KY (US)

(72) Inventor: Frank Castro, Louisville, KY (US)

(73) Assignee: BLUE SKY TECHNOLOGIES, LLC, Louisville, KY (US)

(*) Notice: Subject to any disclaimer, the term of this patent is extended or adjusted under 35 U.S.C. 154(b) by 0 days.

(21) Appl. No.: 16/097,245

(22) PCT Filed: Apr. 3, 2018

(86) PCT No.: PCT/US2018/025785
§ 371 (c)(1),
(2) Date: Oct. 27, 2018

(87) PCT Pub. No.: WO2019/018014
PCT Pub. Date: Jan. 24, 2019

(65) Prior Publication Data
US 2020/0046513 A1 Feb. 13, 2020

Related U.S. Application Data

(60) Provisional application No. 62/534,155, filed on Jul. 18, 2017.

(51) Int. Cl.
*A61F 2/44* (2006.01)
*A61F 2/46* (2006.01)
*A61B 17/70* (2006.01)
*A61F 2/30* (2006.01)
*A61F 2/42* (2006.01)
(Continued)

(52) U.S. Cl.
CPC .......... *A61F 2/447* (2013.01); *A61B 17/7002* (2013.01); *A61B 17/7059* (2013.01); *A61F 2/44* (2013.01); *A61F 2/4405* (2013.01); *A61F 2/4455* (2013.01); *A61F 2/4603* (2013.01); *A61F 2/4611* (2013.01); *A61B 17/1671* (2013.01); *A61B 2017/00884* (2013.01); *A61F 2/42* (2013.01); *A61F 2/4606* (2013.01); *A61F 2002/30179* (2013.01); *A61F 2002/30266* (2013.01); *A61F 2002/30364* (2013.01); *A61F 2002/30579* (2013.01); *A61F 2002/30593* (2013.01); *A61F 2002/30622* (2013.01); *A61F 2002/30736* (2013.01); *A61F 2002/30845* (2013.01); *A61F 2002/30995* (2013.01); *A61F 2002/449* (2013.01);
(Continued)

(58) Field of Classification Search
CPC .......... A61F 2/4455; A61F 2002/30261; A61F 2002/30266; A61F 2002/30271; A61F 2/44–447
See application file for complete search history.

(56) References Cited

U.S. PATENT DOCUMENTS

5,683,394 A * 11/1997 Rinner .................. A61F 2/4455
606/247
5,800,547 A * 9/1998 Schafer .................. A61F 2/442
623/17.16
(Continued)

*Primary Examiner* — Eduardo C Robert
*Assistant Examiner* — Michelle C Eckman
(74) *Attorney, Agent, or Firm* — Business Patent Law, PLLC; Kenneth F. Pearce (57) ABSTRACT

A joint arthrodesis system adapted for use in joint surgeries. Among other things, the joint implant has an anterior cutting edge and a rotatable cutter supported by a rotatable shaft.

20 Claims, 6 Drawing Sheets

(51) Int. Cl.
  *A61B 17/16* (2006.01)
  *A61B 17/00* (2006.01)
(52) U.S. Cl.
  CPC .......... *A61F 2002/4627* (2013.01); *A61F 2310/00017* (2013.01); *A61F 2310/00023* (2013.01)

(56) References Cited

U.S. PATENT DOCUMENTS

| | | | |
|---|---|---|---|
| 6,767,367 B1* | 7/2004 | Michelson | A61F 2/4455 623/17.11 |
| 6,770,096 B2 | 8/2004 | Bolger | |
| 6,824,564 B2 | 11/2004 | Crozet | |
| 6,981,975 B2 | 1/2006 | Michelson | |
| 7,594,932 B2 | 9/2009 | Aferzon et al. | |
| 7,744,649 B2* | 6/2010 | Moore | A61B 17/15 606/86 A |
| 7,988,709 B2* | 8/2011 | Clark | A61B 17/025 606/246 |
| 8,080,062 B2* | 12/2011 | Armstrong | A61F 2/4465 623/17.11 |
| 8,100,972 B1* | 1/2012 | Bruffey | A61F 2/4465 623/17.11 |
| 8,292,958 B1* | 10/2012 | Bruffey | A61F 2/442 606/246 |
| 8,366,774 B1 | 2/2013 | Bruffey et al. | |
| 8,382,843 B2 | 2/2013 | Laurence et al. | |
| 8,545,562 B1* | 10/2013 | Materna | A61F 2/442 623/17.11 |
| 8,617,245 B2* | 12/2013 | Brett | A61F 2/442 623/17.16 |
| 8,795,368 B2* | 8/2014 | Trieu | A61F 2/442 623/17.11 |
| D742,517 S * | 11/2015 | Schifano | D24/155 |
| 9,198,764 B2* | 12/2015 | Greenberg | A61F 2/442 |
| 9,198,774 B2* | 12/2015 | Pisharodi | A61F 2/447 |
| 9,517,144 B2* | 12/2016 | McAtamney | A61F 2/4455 |
| 9,539,110 B2 | 1/2017 | Bergey | |
| 9,566,165 B2* | 2/2017 | Lee | A61F 2/4425 |
| 9,642,721 B2* | 5/2017 | Patterson | A61F 2/4455 |
| 9,987,142 B2* | 6/2018 | McConnell | A61F 2/4455 |
| 10,159,582 B2* | 12/2018 | Gamache | A61F 2/442 |
| 10,342,674 B2* | 7/2019 | Bruffey | A61F 2/4465 |
| 2003/0181981 A1* | 9/2003 | Lemaire | A61F 2/442 623/17.11 |
| 2003/0187436 A1* | 10/2003 | Bolger | A61B 17/0206 623/17.11 |
| 2005/0033429 A1* | 2/2005 | Kuo | A61F 2/447 623/17.11 |
| 2005/0049590 A1* | 3/2005 | Alleyne | A61F 2/442 623/17.11 |
| 2007/0118220 A1* | 5/2007 | Liu | A61F 2/447 623/17.11 |
| 2007/0270961 A1 | 11/2007 | Ferguson | |
| 2008/0027550 A1* | 1/2008 | Link | A61B 17/1671 623/17.16 |
| 2008/0132949 A1* | 6/2008 | Aferzon | A61F 2/446 606/246 |
| 2008/0255666 A1* | 10/2008 | Fisher | A61B 17/7064 623/17.16 |
| 2009/0054988 A1* | 2/2009 | Hess | A61B 17/025 623/17.16 |
| 2009/0099601 A1* | 4/2009 | Aferzon | A61F 2/4455 606/246 |
| 2009/0164020 A1* | 6/2009 | Janowski | A61F 2/4465 623/17.16 |
| 2009/0265007 A1* | 10/2009 | Colleran | A61F 2/4455 623/17.16 |
| 2010/0185289 A1* | 7/2010 | Kirwan | A61F 2/4455 623/17.11 |
| 2011/0035007 A1* | 2/2011 | Patel | A61F 2/4465 623/17.11 |
| 2011/0208311 A1* | 8/2011 | Janowski | A61F 2/4465 623/17.16 |
| 2012/0046748 A1* | 2/2012 | Weiman | A61F 2/44 623/17.16 |
| 2012/0150300 A1* | 6/2012 | Nihalani | A61F 2/442 623/17.16 |
| 2012/0303124 A1* | 11/2012 | McLuen | A61F 2/4611 623/17.16 |
| 2013/0018472 A1* | 1/2013 | Yue | A61F 2/447 623/17.16 |
| 2013/0268076 A1* | 10/2013 | Carlson | A61F 2/446 623/17.16 |
| 2014/0052260 A1* | 2/2014 | McKenny | A61F 2/447 623/17.16 |
| 2014/0094918 A1* | 4/2014 | Vishnubholta | A61F 2/4455 623/17.16 |
| 2014/0114416 A1* | 4/2014 | Zimmerman | A61F 2/44 623/17.16 |
| 2014/0114421 A1 | 4/2014 | Ullrich, Jr. et al. | |
| 2014/0121773 A1* | 5/2014 | Patel | A61F 2/4455 623/17.16 |
| 2014/0172104 A1* | 6/2014 | Dugal | A61F 2/4611 623/17.16 |
| 2015/0100127 A1* | 4/2015 | Bal | A61F 2/4455 623/17.16 |
| 2015/0127107 A1* | 5/2015 | Kim | A61F 2/447 623/17.16 |
| 2015/0173917 A1* | 6/2015 | Radcliffe | A61F 2/4455 623/17.16 |
| 2015/0265416 A1 | 9/2015 | Aferzon et al. | |
| 2015/0305880 A1* | 10/2015 | Kim | A61F 2/4611 623/17.16 |
| 2016/0000578 A1* | 1/2016 | Bae | A61B 17/846 623/17.16 |
| 2016/0113781 A1* | 4/2016 | Laurence | A61F 2/30767 623/17.16 |
| 2016/0374831 A1* | 12/2016 | Duffield | A61F 2/4611 623/17.16 |
| 2017/0135822 A1* | 5/2017 | Bender | A61F 2/30749 |
| 2017/0165082 A1* | 6/2017 | Faulhaber | A61F 2/4455 |
| 2017/0340453 A1* | 11/2017 | Kaufmann | A61F 2/4611 |
| 2017/0360571 A1* | 12/2017 | Mesiwala | A61F 2/447 |
| 2018/0104068 A1* | 4/2018 | Sack | A61F 2/4455 |
| 2018/0110627 A1* | 4/2018 | Sack | A61F 2/4611 |
| 2018/0296359 A1* | 10/2018 | Sack | A61F 2/4465 |
| 2019/0224017 A1* | 7/2019 | Grim | A61F 2/442 |
| 2019/0314171 A1* | 10/2019 | Castro | A61F 2/4603 |

\* cited by examiner

Section A-A

JOINT ARTHRODESIS SYSTEM

Applicant claims priority to PCT Application entitled—Joint Arthrodesis System—, Serial No. PCT/US2018/025785, filed Apr. 3, 2018 that claimed priority to US provisional Patent Application entitled—Joint Arthrodesis System—, Ser. No. 62/534,155, filed Jul. 18, 2017.

BACKGROUND OF THE INVENTION

A. Field of the Invention

The present invention is a joint arthrodesis system. Among other things, the implant of the current system has a cutting edge as well as a rotatable cutter.

B. Description of the Previous Art

Any discussion of references cited in this Description of the Previous Art merely summarizes the disclosures of the cited references and Applicant makes no admission that any cited reference or portion thereof is relevant prior art. Applicant reserves the right to challenge the accuracy, relevancy and veracity of the cited references.

1) U.S. Pat. No. 6,770,096-Bolger, et al. discloses an interbody spinal stabilization cage and spinal stabilization method. Among other things, Bolger does not disclose a framework comprising: an anterior side comprising a cutting edge; a rotatable shaft extending between the cutting edge and the surgeon facing side; and a first arm connected with the shaft; the first arm supporting a first cutter comprising one or more blades, wherein on rotation of the shaft, the blades cut in a clockwise or counterclockwise direction.

2) U.S. Pat. No. 6,824,564-Crozet discloses a two-part intersomatic implant. Among other things, Crozet does not disclose a framework comprising: an anterior side comprising a cutting edge; a rotatable shaft extending between the cutting edge and the surgeon facing side; and a first arm connected with the shaft; the first arm supporting a first cutter comprising one or more blades, wherein on rotation of the shaft, the blades cut in a clockwise or counterclockwise direction.

3) U.S. Pat. No. 6,981,975-Michelson discloses a method for inserting a spinal fusion implant having deployable bone engaging projections. Among other things, Michelson does not disclose a framework comprising: an anterior side comprising a cutting edge; a rotatable shaft extending between the cutting edge and the surgeon facing side; and a first arm connected with the shaft; the first arm supporting a first cutter comprising one or more blades, wherein on rotation of the shaft, the blades cut in a clockwise or counterclockwise direction.

4) U.S. Pat. No. 7,594,932-Aferzon, et al. enables an apparatus for anterior intervertebral spinal fixation and fusion. Among other things, Aferzon does not disclose a framework comprising: an anterior side comprising a cutting edge; a rotatable shaft extending between the cutting edge and the surgeon facing side; and a first arm connected with the shaft; the first arm supporting a first cutter comprising one or more blades, wherein on rotation of the shaft, the blades cut in a clockwise or counterclockwise direction.

5) U.S. Pat. No. 8,366,774-Bruffey, et al. discloses an apparatus for anterior intervertebral spinal fixation and fusion. Among other things, Bruffey does not disclose a framework comprising: an anterior side comprising a cutting edge; a rotatable shaft extending between the cutting edge and the surgeon facing side; and a first arm connected with the shaft; the first arm supporting a first cutter comprising one or more blades, wherein on rotation of the shaft, the blades cut in a clockwise or counterclockwise direction.

6) U.S. Pat. No. 8,382,843-Laurence, et al. discloses an intervertebral implant with blades for connecting to adjacent vertebral bodies. Among other things, Laurence does not disclose a framework comprising: an anterior side comprising a cutting edge; a rotatable shaft extending between the cutting edge and the surgeon facing side; and a first arm connected with the shaft; the first arm supporting a first cutter comprising one or more blades, wherein on rotation of the shaft, the blades cut in a clockwise or counterclockwise direction.

7) U.S. Pat. No. 9,539,110-Bergey discloses an interbody prosthetic device with compound-arc, blade anchor. Among other things, Bergey does not disclose a framework comprising: an anterior side comprising a cutting edge; a rotatable shaft extending between the cutting edge and the surgeon facing side; and a first arm connected with the shaft; the first arm supporting a first cutter comprising one or more blades, wherein on rotation of the shaft, the blades cut in a clockwise or counterclockwise direction.

8) US Published Patent Application No. 20070270961-Ferguson discloses a spinal implant deployable with retractable barbs. Among other things, Ferguson does not disclose a framework comprising: an anterior side comprising a cutting edge; a rotatable shaft extending between the cutting edge and the surgeon facing side; and a first arm connected with the shaft; the first arm supporting a first cutter comprising one or more blades, wherein on rotation of the shaft, the blades cut in a clockwise or counterclockwise direction.

9) US Published Patent Application No. 20080027550-Link, et al. discloses a cervical intervertebral disc prosthesis comprising an anti-dislocation device and instruments. Among other things, Link does not disclose a framework comprising: an anterior side comprising a cutting edge; a rotatable shaft extending between the cutting edge and the surgeon facing side; and a first arm connected with the shaft; the first arm supporting a first cutter comprising one or more blades, wherein on rotation of the shaft, the blades cut in a clockwise or counterclockwise direction.

10) US Published Patent Application No. 20140121773-Patel, et al. discloses a stand-alone interbody fixation system. Among other things, Patel does not disclose a framework comprising: an anterior side comprising a cutting edge; a rotatable shaft extending between the cutting edge and the surgeon facing side; and a first arm connected with the shaft; the first arm supporting a first cutter comprising one or more blades, wherein on rotation of the shaft, the blades cut in a clockwise or counterclockwise direction.

11) US Published Patent Application No. 20160374831-Duffield, et al. discloses an interbody fusion device and system for implantation. Among other things, Duffield does not disclose a framework comprising: an anterior side comprising a cutting edge; a rotatable shaft extending between the cutting edge and the surgeon facing side; and a first arm connected with the shaft; the first arm supporting a first cutter comprising one or more blades, wherein on rotation of the shaft, the blades cut in a clockwise or counterclockwise direction.

12) WIPO Published Patent Application No. 2007/079021-Aferzon, et al. discloses an apparatus for anterior intervertebral spinal fixation and fusion. The Specification of WIPO Published Patent Application No. 2007/079021-Aferzon, et al. is similar to U.S. Pat. No. 7,594,932-Aferzon, et al. Therefore, among other things, Aferzon does not disclose a framework comprising: an anterior side comprising a cutting edge; a rotatable shaft extending between the cutting edge and the surgeon facing side; and a first arm connected with the shaft; the first arm supporting a first cutter comprising one or more blades, wherein on rotation of the shaft, the blades cut in a clockwise or counterclockwise direction.

SUMMARY OF THE INVENTION

The more tools or instruments inserted into a surgical field, the greater the possibility of an error or patient injury may occur. Due to the simplicity of the current joint arthrodesis system, a number of surgical tools required and steps associated with performing prior state-of-the-art fusions can be eliminated. The arthrodesis procedures, among other uses, can be performed in the cervical spine, sacroiliac joint, ankle, hand or other similar joints.

One of the currently available state-of-the art techniques for cervical fusions is the DTRAX system. The DTRAX spinal system uses five instruments, a working cannula, and numerous steps. A working cannula with a chisel is used to breach the desired posterior facet joint. Once in position, the chisel is removed and a broach is inserted through the working cannula. The broach is advanced and retracted several times in order to remove the cartilaginous end-plates. After the broach is removed from the working cannula, a drill is inserted. After drilling is completed, a second rasp is placed to decorticate the posterior cortex. After the use of the second rasp is completed, the fixation device (filled with graft material) is inserted through the working cannula into the joint. Additional graft material is then impacted behind the implant.

Current state-of-the-art sacroiliac surgical procedures require a fusion device that is either inserted from a posterior or lateral approach. Applicant's understanding is: there are fusion devices for use with either the posterior approach or the lateral approach, but the same fusion device is incapable for use with both the posterior and the lateral approaches. Many of the current sacroiliac fusion procedures require the use of working cannulas, numerous broaches, rasps, drills and other devices that tend to complicate the surgical procedure. Applicant's current joint arthrodesis system can accomplish sacroiliac fusions through either a posterior or lateral approach with fewer surgical tools and steps.

Unlike other joint arthrodesis systems, the present system's joint arthrodesis implant includes a cutting edge and one or more rotatable cutters including one or more blades. Among other things, it is believed that the cutters can assist with the postoperative stabilization of the joint implant. In accordance with the current invention, rotation of a blade about 90 degrees allows the blade to extend beyond the joint implant's framework and penetrate adjacent cartilage and bone.

An aspect of the present invention is to provide a joint implant with an anterior side having a cutting edge.

Still another aspect of the present invention is to provide a joint implant with a rotatable shaft extending from the surgeon facing side having to anterior side.

It is still another aspect of the present invention to provide a joint implant with one or more rotatable cutters affixed to the shaft, where each cutter can include one or more blades.

Yet still another aspect of the present invention is to provide a joint implant where rotation of the rotatable cutter causes one or more of the cutters to extend beyond the framework.

Still another aspect of the present invention is to provide a joint implant with rotatable cutters for cutting in the clockwise or counterclockwise directions.

Yet another aspect of the present invention is to provide a joint implant with one or more recesses capable of receiving one or more cutters, for example, when the implant is utilized in its insertion mode.

It is still another aspect of the present invention to provide a joint implant where near the completion of the surgical procedure, the joint implant's rotating blades can be rotated to extend beyond the joint implant's framework.

Still another aspect of the present invention is to provide edges on the cutting arms that can assist with the morselization of bone.

A preferred embodiment of the current invention can be described as: a joint arthrodesis system comprising: a) a framework comprising: i) a longitudinal axis, openings outward from the longitudinal axis and a length greater than a width; ii) an anterior side comprising a cutting edge integral with the anterior side; iii) a surgeon facing side at an end opposite the anterior side; the anterior side having a lesser cross-sectional area than a cross-sectional area of the surgeon facing side, wherein the cross-sectional areas are determined perpendicular to the longitudinal axis; iv) a plate seated within the cross-sectional area of the surgeon facing side and affixed to the framework, wherein the plate is perpendicular to the longitudinal axis and comprises one or more apertures capable of reciprocating with one or more instruments; v) a shaft aligned with the longitudinal axis and extending between an inner side of the plate and the cutting edge; and vi) arms connected with the shaft; the arms supporting cutters comprising one or more blades, wherein on rotation of the shaft, the one or more blades cut in a clockwise or counterclockwise direction; and b) a tool capable of rotating the shaft.

Another preferred embodiment of the current invention can be described as: a joint implant comprising: a) a framework comprising: i) a longitudinal axis, openings outward from the longitudinal axis and a length greater than a width; ii) an anterior side comprising a cutting edge; iii) a surgeon facing side at an end opposite the anterior side, wherein the surgeon facing side is perpendicular to the longitudinal axis and comprises one or more apertures capable of reciprocating with one or more instruments; iv) a shaft aligned with the longitudinal axis and extending between an inner side of the surgeon facing side and the cutting edge; and v) one or more arms connected with the shaft; the one or more arms supporting one or more cutters comprising one or more blades, wherein on rotation of the shaft, one or more blades cut in a clockwise or counterclockwise direction.

Still another preferred embodiment of the current invention can be described as: a joint implant comprising: a) a framework comprising: i) a longitudinal axis and openings outward from the longitudinal axis; ii) an anterior side comprising a cutting edge; iii) a surgeon facing side at an end opposite the anterior side; the surgeon facing side comprising one or more apertures; iv) a rotatable shaft extending between the cutting edge and the surgeon facing side; and v) a first arm connected with the shaft; the first arm supporting a first cutter comprising one or more blades, wherein on rotation of the shaft, the blades cut in a clockwise or counterclockwise direction.

It is the novel and unique interaction of these simple elements which creates the system within the ambit of the present invention. Pursuant to the Articles of the Patent Cooperation Treaty, select preferred embodiments of the current invention follow. However, it is to be understood that the descriptions of the preferred embodiments do not limit the scope of the present invention.

DESCRIPTION OF THE PREFERRED EMBODIMENTS

Although the disclosure hereof is detailed to enable those skilled in the art to practice the invention, the embodiments published herein merely exemplify the present invention.

As used herein, with respect to the joint arthrodesis system's implant: 1) "anterior" of the joint implant means the side of the implant most distant from the surgeon and 2) "posterior or surgeon-facing side" of the joint implant means the side of the implant nearest the surgeon.

In the most general sense, the present invention is a joint arthrodesis system where an implant is surgically inserted into a joint space. The current implant can be useful for surgeries that can assist in stabilizing injured, deformed and or degenerative joints. Preferred embodiments of the current invention can be employed with ankle, cervical, hand, sacroiliac or other orthopaedic procedures. It appears that the present system is particularly useful for posterior cervical fusions and sacroiliac joint fusions. However, the current invention can also be used to fuse the tibia to the talus, the talus to the calcaneus, and metacarpals to the phalanges.

Preferred embodiments of the current joint implants can be manufactured of titanium alloys, stainless steel, resorbable polymers, non-resorbable polymers or any other composition acceptable in the art. Meeting a long felt but unfilled need in the orthopaedic surgical arts, the novel and unique structures of the present combinations allow the surgical team to, among other things, simplify previous procedures.

The present invention has a cutting edge and a rotatable cutter including one or more blades. The cutting edge of the implant's framework is capable of dissecting through adipose, muscle and/or joint capsule tissues. The rotatable cutter of the implant is capable of cutting cartilage and bone and can be associated with the creation of the surgical cavity. Further, the rotatable cutter can morselize bone in preparation for fusion. The combination of the cutting edge(s) and rotatable cutter of the current joint implant system meet long felt but unfilled needs in the orthopedic surgical arts: among other things, these novel and unique structures allow the surgeon to simplify the previous operating procedures utilized for posterior cervical, sacroiliac, and other joint fusions.

Devices that insert osteogenic and/or other substances into the interior volume of the implant can be used with the present invention. The current joint arthrodesis system is also compatible with flexible drills, fiber optics, vacuums, one or more cannulas and one or more devices for inserting the joint implant. Combinations of one or more of the before identified ancillary devices and the current joint arthrodesis system can assist with the creation and healing of the surgical wound.

Openings of the current joint implant increase the probability of the osteogenic materials and/or arthrodesis accelerating substances procuring a blood supply. And it is believed that increasing the blood supply to the osteogenic materials held by the joint implant or implant increases the probability of successful fusion. Introduction of osteogenic and other substances into the implant can hasten the healing of the surgical wound.

Figure 1:
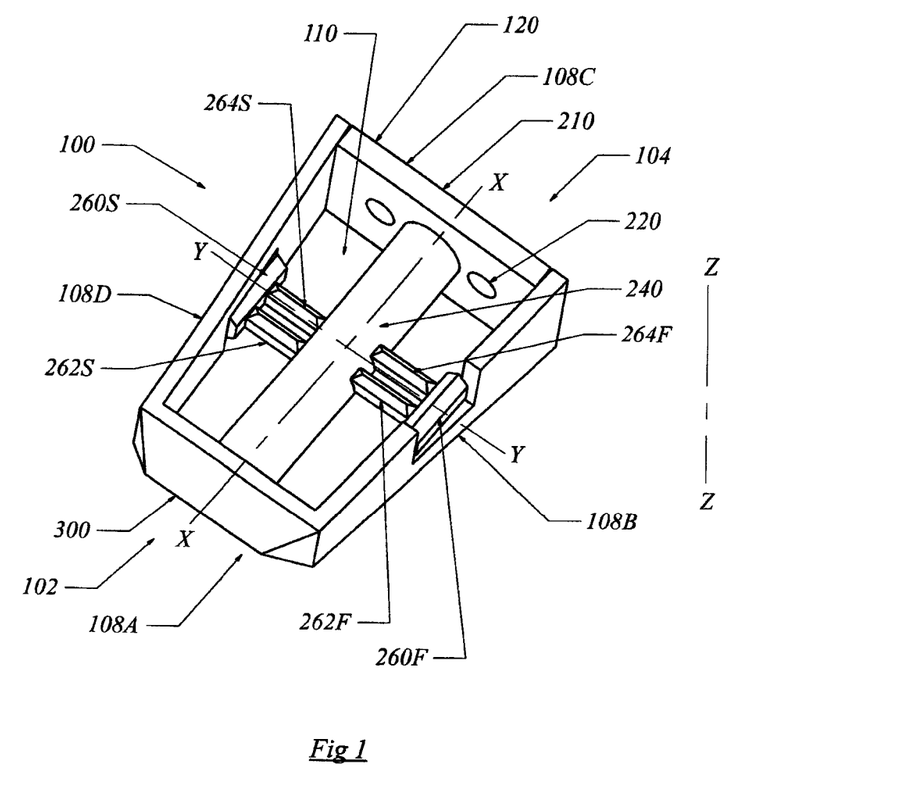
FIG. 1 is a perspective of a preferred embodiment of the joint implant (100) utilized in the present system.

FIG. 1 is a perspective of a preferred embodiment of the joint implant (100) utilized in the present system. Joint implant or implant (100) has a framework that includes an anterior side (102), surgeon facing or posterior side (104) and a plurality of lengthwise sides (108A-D) extending between anterior side (102) and surgeon facing or posterior side (104). Lengthwise sides (108A, 108C) are provided with opening (110) that, among other things, allows the implant's blades to rotate. When surgical parameters require, osteogenic and/or other substances can also be placed into the internal volume of implant (100).

With respect to this application, the longitudinal axis of joint implant (100) is measured along axis X-X. Axis X-X can correspond with shaft (240) or in some preferred embodiments shaft (240) can be offset from axis X-X. Width of implant (100) is measured along axis Y-Y or an axis parallel to axis Y-Y shown in FIG. 1. Height of joint implant is measured along axis Z-Z or an axis parallel to axis Z-Z of the joint implant's framework.

Within the scope of the current invention, select embodiments of implant (100) have a length greater than a width. In select preferred embodiments, the width of implant (100) is greater than the height of implant (100). In other preferred embodiments of implant (100), the height of implant (100) is greater than the width of implant (100). The inward sides of anterior side (102), posterior side (104) and lengthwise sides (108A-D) facing longitudinal axis X-X create an available inner volume of implant (100) which can receive osteogenic as well as other substances.

Lengthwise or lateral sides (108A-108D) are positioned outward from joint implant's (100) longitudinal axis X-X. Select preferred embodiments of implant (100) are provided with a cross-section distant from anterior side (102) that has a greater cross-sectional area than the anterior side (102). As disclosed herein, cross-sections are determined perpendicular to the longitudinal axis X-X of the implant's framework. Anterior side (102) of implant (100) is provided with cutting edge (300) as will be more specifically enabled below. In some preferred embodiments, cutting edge (300) can be integral with anterior side (102) of joint implant (100). Attached to shaft (240) are arms (262F, 262S) supporting cutters (260F, 260S). Although as shown in FIG. 1, cutters (260F, 260S) are supported by two arms (262F, 262S), in select preferred embodiments, cutters (260F, 260S) can be supported by a single arm (262F, 262S). Additionally, some preferred embodiments of cutters (260F, 260S) can be provided with one or more sharp edges (264F, 264S) that can assist cutters (260F, 260S) with the morselization of bone.

Posterior side (104) of implant (100) includes cross-sectional area (120). Preferred embodiments of joint implant (100) are provided with plate (210) where at least a portion the plate (210) is perpendicular to longitudinal axis X-X. Plate (210) is seated within cross-sectional area (120) of surgeon facing side (104) and affixed to implant (100). Preferred embodiments of plate (210) are provided with one or more apertures (220) that can be utilized with one or more tools associated with the surgery.

Figure 2:
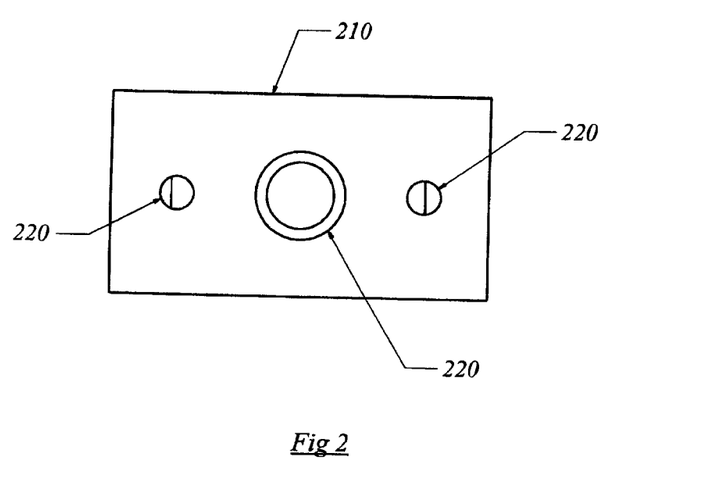
FIG. 2 is a frontal view of plate (210) seated in cross-sectional area (120) of surgeon facing side (104) of implant (100).

FIG. 2 is a frontal view of plate (210) seated in cross-sectional area (120) of surgeon facing side (104) of implant (100). As shown, cross-sectional area is provided with a plurality of openings (220).

Figures 3, 4:
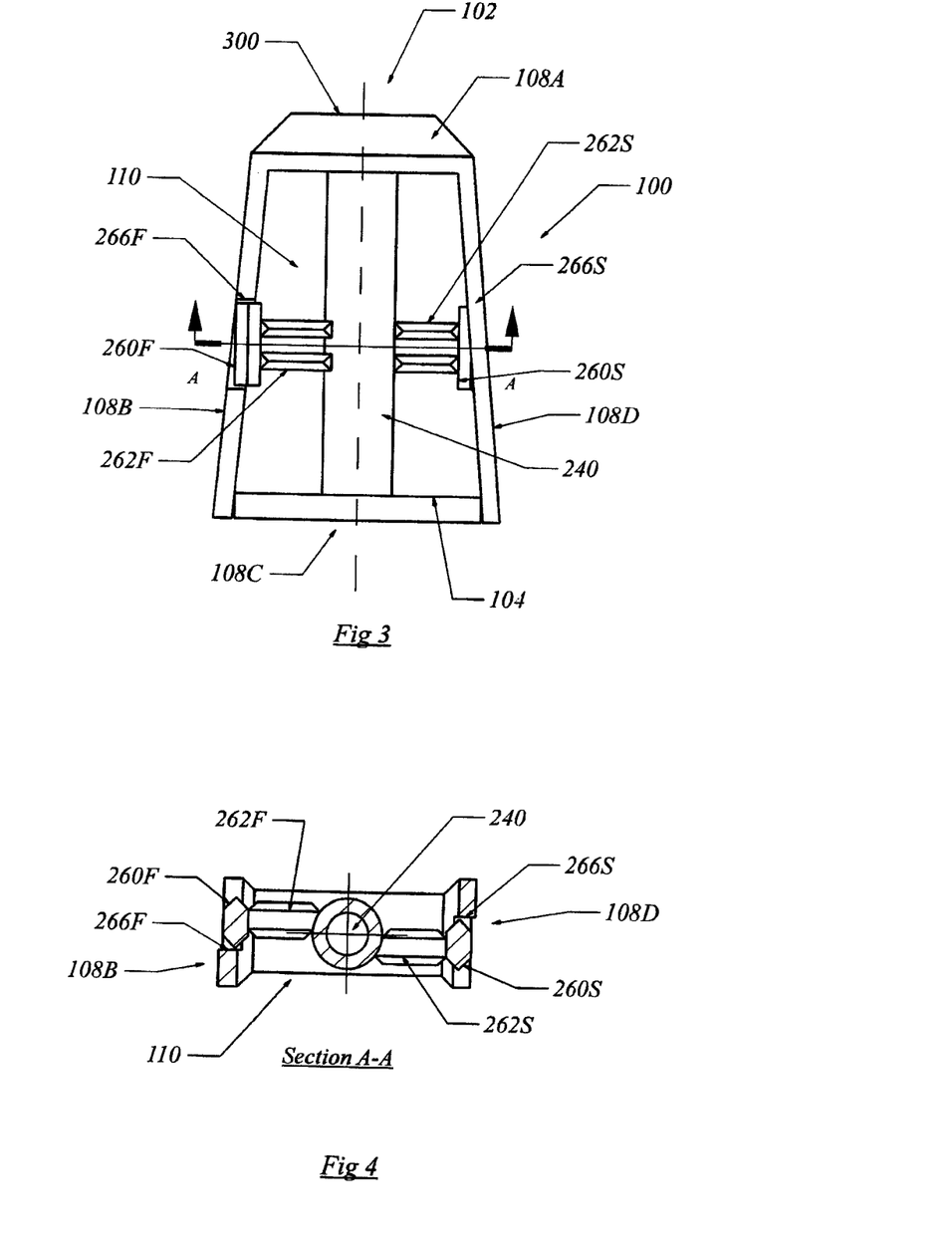
FIG. 3 is a top view of implant (100).
FIG. 4 is a frontal view cross-section of implant (100) along section A-A as seen from the posterior side (104).

FIG. 3 is a top view of implant (100), where implant is shown in its subcutaneous surgical wound creation mode. Shaft (240) is connected with anterior end (102) and surgeon posterior side (104) in any manner acceptable in the art. Proximate shaft (240) is opening (110) and lateral sides (108A-108D). First arms (262F) attach first cutter (260F) to shaft (240). Second arms (262S) attach second cutter (260S) to shaft (240). Cutters (260F and 260S) can be provided with blades that cut in both the clockwise and counterclockwise directions when shaft (240) is rotated. Lateral side (108B) is provided with recess (266F) capable of receiving cutter (260F). Lateral side (108D) is provided with recess (266S) capable of receiving cutter (260S). As shown in FIG. 3, recess (266F) is located on the superior side of lengthwise side (108B) and recess (266S) is positioned on the inferior side of lengthwise side (108D).

FIG. 4 is a frontal view cross-section of implant (100) along section A-A as seen from the posterior side (104). Cutter (260F) is received in recess (266F) of lateral side (108B) and arms (262F) attach cutter (260F) to shaft (240). Cutter (260S) is received in recess (266S) of lateral side (108D) and arms (262S) attach cutter (260S) to shaft (240). Within the scope of the current invention, cutters (260F, 260S) can be supported by a single arm (262F, 262S). And when surgical parameters require, implant (100) is engineered with only a single cutter (260F).

Figure 5:
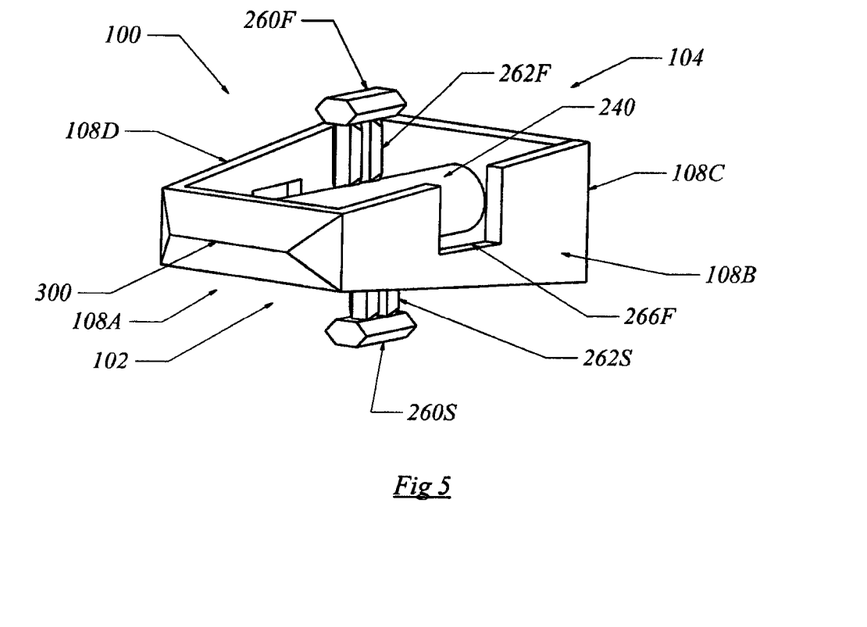
FIG. 5 is a perspective of implant (100).

FIG. 5 is a perspective of a preferred embodiment of implant (100). Shaft (240) extends from cutting edge (300) toward surgeon facing side (104) of implant (100). As shown in FIG. 5, shaft (240) has rotatable arms (262F, 262S) carrying cutters (260F, 260S) such that rotation of shaft (240) extends cutter (260F) beyond lateral side (108C) and cutter (260S) beyond lateral side (108A) of implant (100).

Figure 6:
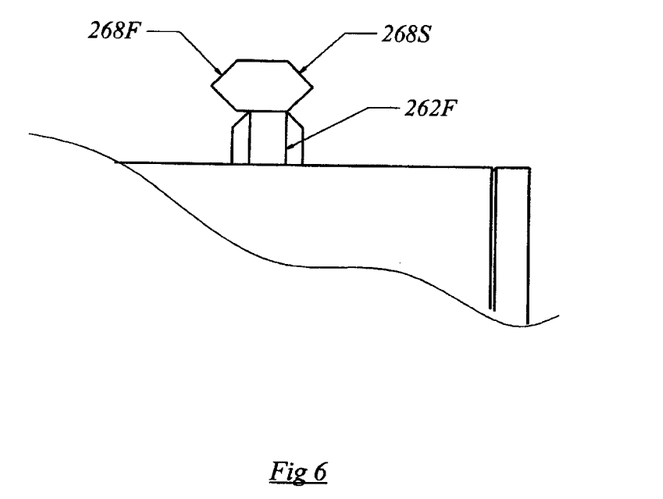
FIG. 6 is a frontal view of a preferred embodiment of cutter (260F) shown in FIG. 5 as seen from the anterior side of implant (100).

FIG. 6 is a frontal view of a preferred embodiment of cutter (260F) shown in FIG. 5 as seen from the anterior side of implant (100). Cutter (260F) is provided with first and second cutting blades (268F, 268S) that allow cutter (260F) to cut in both the clockwise and counterclockwise directions. Depending on engineering parameters cutters (260F, 260S) can be equipped with one or more cutting blades. Along with the cutting function of cutters (260F, 260S), near the conclusion of the surgical procedure, cutting blades (268F, 268S) can be rotated to cut into bone so that cutters (260F, 260S) further anchor the implant (100) within the joint space.

Figure 7:
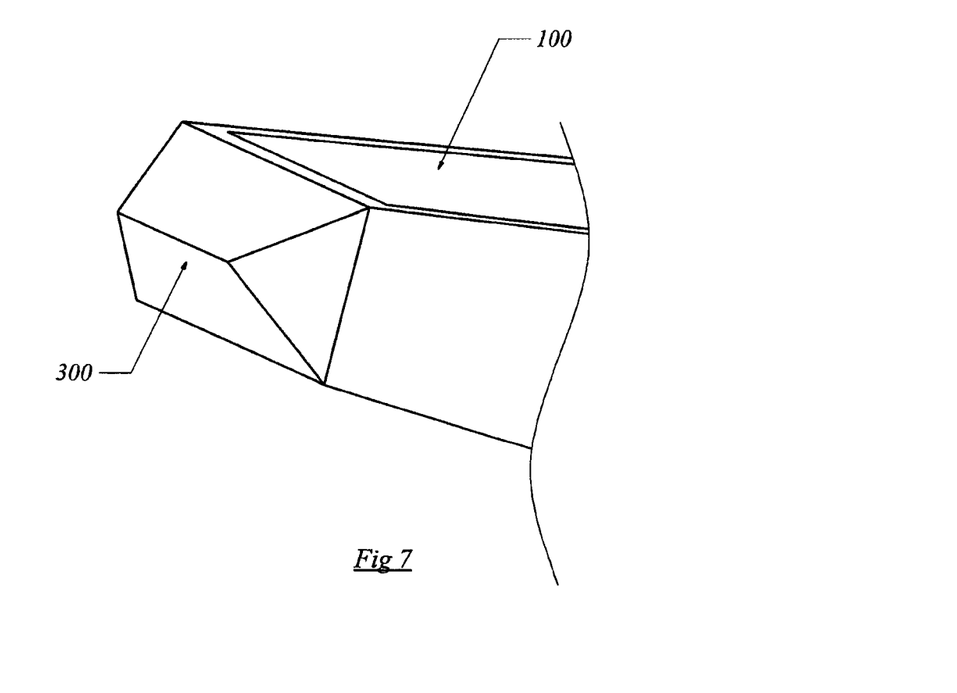
FIG. 7 is a perspective of cutting edge (300) of implant (100).

FIG. 7 is a perspective of cutting edge (300) of implant (100). Cutting edge (300) can be integral with implant (100) or cutting edge (300) can be manufactured as an interchangeable fitting for implant (100). Within the ambit of the current joint arthrodesis system, cutting edges (300) are capable of dissecting through adipose, muscle and/or joint capsule tissues.

Figure 8:
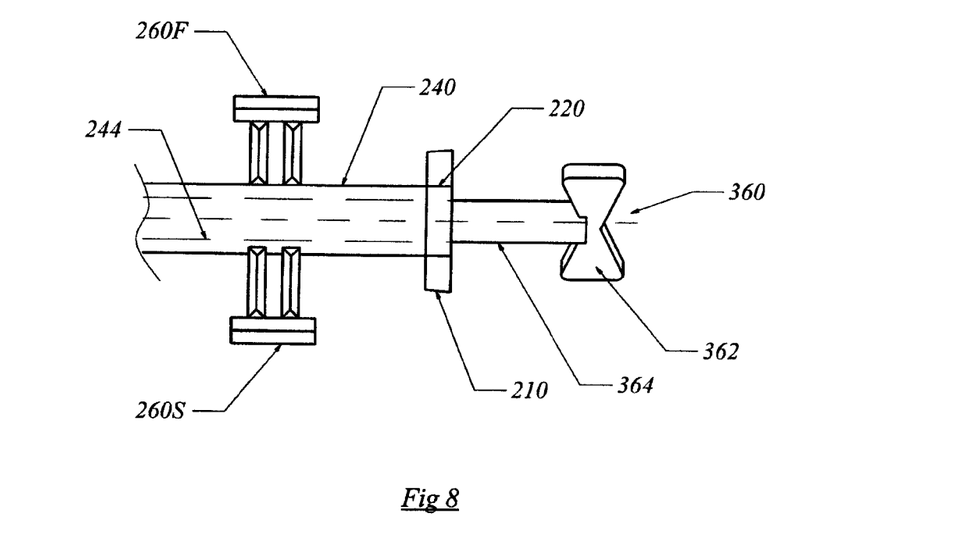
FIG. 8 is a lateral view as seen from side (108B) with lateral sides (108A-D) of implant (100) cut away.

FIG. 8 is a lateral view as seen from side (108B) with lateral sides (108A-D) of implant (100) cut away. Plate (210) includes aperture (220) capable of receiving hand tool (360). Hand tool (360) includes handle (362) and stem (364) that extends from handle (362). Shaft (240) includes receptacle (244) for reciprocating with stem (364) of hand tool (360). Interaction between stem (364) and receptacle (244) allows hand tool (360) to rotate cutters (260F, 260S) in both clockwise and counterclockwise directions. In select preferred embodiments receptacle (244) can extend the entire length of (240) for allowing ingress and egress of surgical appliances and instruments from the surgical field, e.g., wires, cannulas, vacuum tubes, fiber optics, etc.

Figure 9:
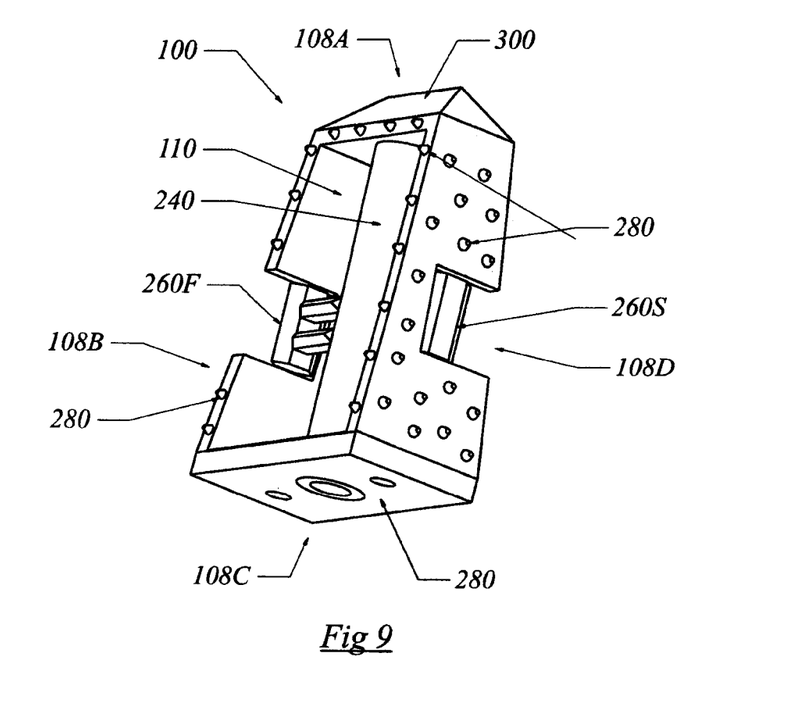
FIG. 9 is a perspective of a preferred embodiment of implant (100).

FIG. 9 is a perspective of a preferred embodiment of implant (100) that depicts cutting edge (300), rotatable cutters (260F, 260S) and opening (110) of implant (100). As shown, barbs (280) extend away from surfaces of lengthwise sides (108B, 108C, 108D). It is believed that barbs (280) can assist in deterring movement of implant (100) within the joint space.

Figure 10:
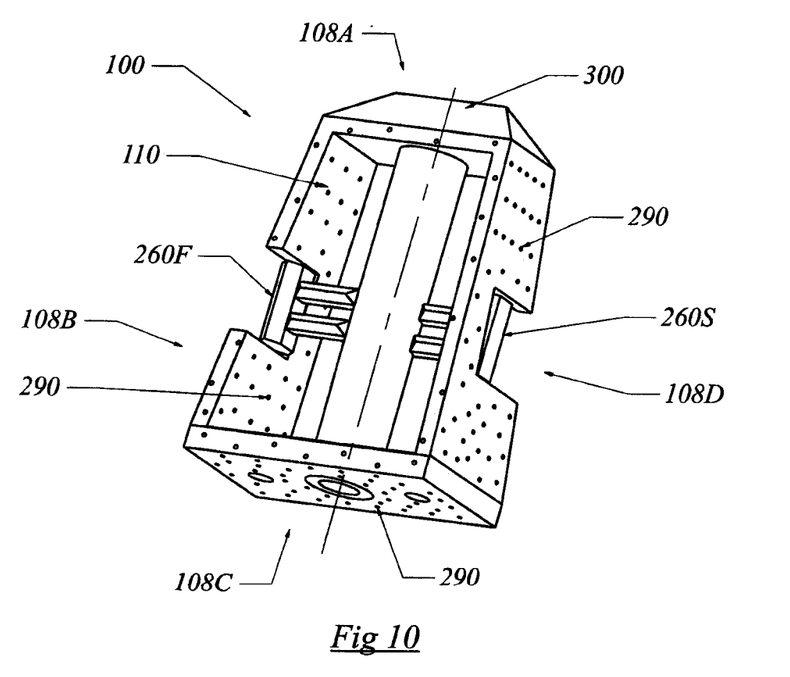
FIG. 10 is a perspective of a preferred embodiment of implant (100).

FIG. 10 is a perspective of a preferred embodiment of implant (100) that depicts cutting edge (300), rotatable cutters (260F, 260S) and opening (110) of implant (100). In the FIG. 10 embodiment, surfaces of lengthwise sides (108B, 108C, 108D) are provided with micropores (290) of various volumes. It is believed that surface micropores (290) can assist with long term fixation of the implant by allowing more bone ingrowth into the implant. In accordance with the FIG. 10 preferred embodiment of spinal implant (100), micropores (290) are generated by surface treatments to at least a portion of surfaces of lengthwise sides (108B, 108C, 108D). Micropores (290) can be created by abrasive, chemical or laser means.

Figure 11:
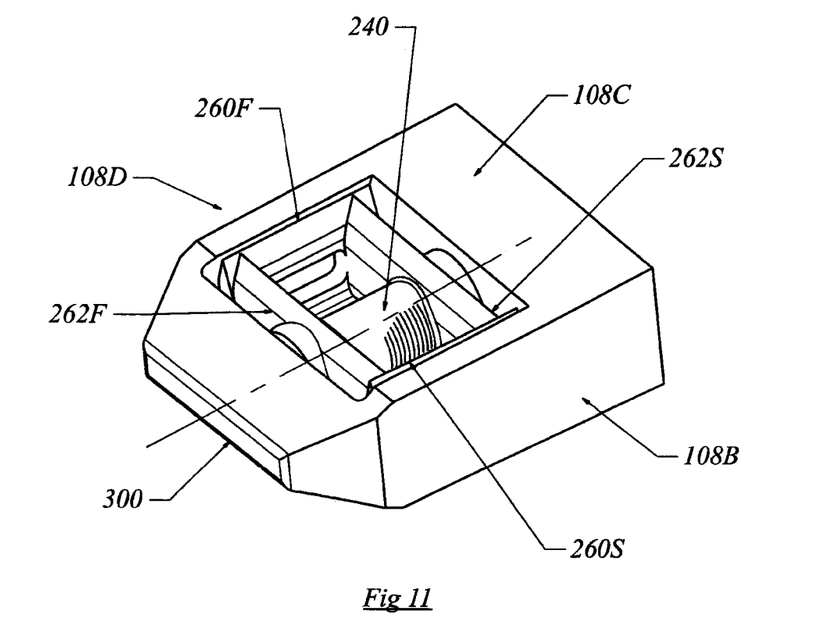
FIG. 11 is a perspective of a preferred embodiment of implant (100) where cutters (260F, 260S) are capable of being rotated 360 degrees about longitudinal axis X-X.

FIG. 11 is a perspective of a preferred embodiment of implant (100) where cutters (260F, 260S) are capable of being rotated 360 degrees about longitudinal axis X-X.

Figure 12:
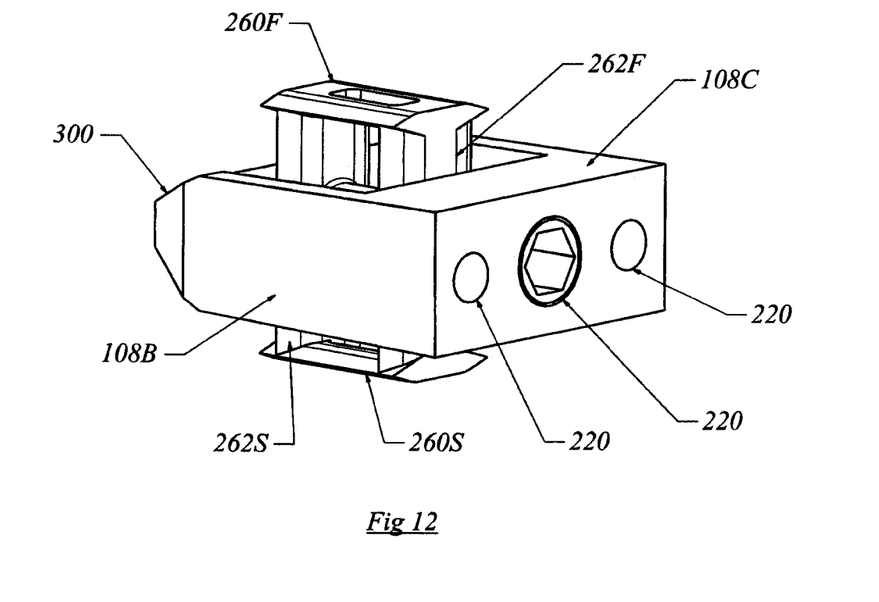
FIG. 12 is another perspective of a preferred embodiment of implant (100) where cutters (260F, 260S) are capable of being rotated 360 degrees about longitudinal axis X-X.

FIG. 12 is another perspective of a preferred embodiment of implant (100) where cutters (260F, 260S) are capable of being rotated 360 degrees about longitudinal axis X-X.

As measured along longitudinal axis X-X of implant's (100) framework, preferred embodiments are provided with cutting edge (300) that can be up to about 3 millimeters in length. The length of implant (100), including cutting edge (300) can be from about 50 millimeters to about 6 millimeters. Cross-sectional widths of cutting edge (300) can range from about 2 millimeters$^2$ to about 18 millimeters$^2$. Cross-sectional widths of implant (100), other than cutting edge (300) can range from about 8 millimeters$^2$ to about 45 millimeters$^2$.

Pursuant to the Articles of the Patent Cooperation Treaty, preferred embodiments of the current system invention have been disclosed and enabled.

What is claimed is:

1. A joint arthrodesis system comprising:
   a) a framework comprising:
      i) a central axis measured in a longest dimension of said framework; said framework including a length greater than a width;
      ii) openings outward from said central axis;
      iii) an anterior side comprising a cutting edge integral with said anterior side;
      iv) a surgeon facing side at an end opposite said anterior side; said anterior side having a lesser cross-sectional area than a cross-sectional area of said surgeon facing side, wherein said cross-sectional areas are determined perpendicular to said central axis;
v) a plate seated within said cross-sectional area of said surgeon facing side and affixed to said framework, wherein said plate is perpendicular to said longitudinal axis and comprises one or more apertures capable of reciprocating with one or more instruments;
vi) a shaft, coaxial with said central axis, extending between an inner side of said plate and said cutting edge; and
vii) arms connected with said shaft; said arms supporting cutters comprising one or more blades, wherein on rotation of said shaft, said one or more blades rotate about said central axis in a clockwise or counterclockwise direction; and
b) a tool capable of rotating said shaft.

2. The joint arthrodesis system of claim 1, wherein said framework comprises four lateral sides.

3. The joint arthrodesis system of claim 2, wherein one or more surfaces of said framework comprises barbs and/or micropores.

4. The joint arthrodesis system of claim 3, wherein said framework comprises recesses adapted to receive said cutters, said recesses positioned diagonally from each other relative to two opposed lateral sides said framework.

5. The joint arthrodesis system of claim 4, wherein outermost ends of said one or more blades extend to outward edges of said recesses.

6. A joint implant comprising a framework; said framework comprising:
a) a central axis measured in a longest dimension of said framework, wherein said framework's length is greater than said framework's width;
b) openings outward from said central axis;
c) an anterior side comprising a cutting edge;
d) a surgeon facing side at an end opposite said anterior side, wherein said surgeon facing side is perpendicular to said central axis and comprises one or more apertures capable of reciprocating with one or more instruments;
e) a shaft, coaxial with said central axis, extending between an inner side of said surgeon facing side and said cutting edge; and
f) one or more arms connected with said shaft; said one or more arms supporting one or more cutters comprising one or more blades, wherein on rotation of said shaft, said one or more blades rotate about said central axis in a clockwise or counterclockwise direction.

7. The joint implant of claim 6, said framework comprising four lateral sides.

8. The joint implant of claim 7, said shaft comprising a receptacle for interacting with a tool capable of rotating said shaft.

9. The joint implant of claim 8, wherein said one or more arms comprise one or more sharp edges adapted to morselize bone.

10. The joint implant of claim 8, wherein one or more surfaces of said framework comprises barbs and/or micropores.

11. The joint implant of claim 8, said framework comprising recesses adapted to receive said cutters, said recesses positioned diagonally from each other relative to two opposed lateral sides said framework.

12. The joint implant of claim 11, wherein said anterior side has a lesser cross-sectional area than a cross-sectional area of said surgeon facing side; said cross-sectional areas determined perpendicular to said central axis.

13. A joint implant comprising a framework; said framework comprising:
a) a central axis measured in a direction of a longest dimension of said framework;
b) openings outward from said central axis;
c) an anterior side comprising a cutting edge; d) a surgeon facing side at an end opposite said anterior side; said surgeon facing side comprising one or more apertures;
e) a rotatable shaft, coaxial with said central axis, extending between said cutting edge and said surgeon facing side; and
f) a first arm connected with said shaft; said first arm supporting a first cutter comprising one or more blades, wherein on rotation of said shaft, said blades rotate about said central axis in a clockwise or counterclockwise direction.

14. The joint implant of claim 13, said framework comprising four lateral sides and a length greater than a width.

15. The joint implant of claim 14, said shaft comprising a receptacle for interacting with a tool capable of rotating said shaft.

16. The joint implant of claim 14, wherein one or more surfaces of said framework comprises barbs and/or micropores.

17. The joint implant of claim 15, wherein said first arm comprises one or more sharp edges adapted to morselize bone.

18. The joint implant of claim 15, said framework further comprising a second arm connected with said shaft; said second arm supporting a second cutter comprising one or more blades, wherein on rotation of said shaft, said blades rotate in a clockwise or counterclockwise direction.

19. The joint implant of claim 18, said framework's anterior side having a lesser cross-sectional area than a cross-sectional area of said surgeon facing side.

20. The joint implant of claim 19, said framework comprising recesses adapted to receive said first and second cutters.

* * * * *